(12) United States Patent
Iwanaga (10) Patent No.: US 8,857,989 B2
(45) Date of Patent: Oct. 14, 2014

(54) OPHTHALMIC APPARATUS AND CONTROL METHOD THEREOF

(75) Inventor: Tomoyuki Iwanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 229 days.

(21) Appl. No.: 13/103,238

(22) Filed: May 9, 2011

(65) Prior Publication Data

US 2011/0292337 A1 Dec. 1, 2011

(30) Foreign Application Priority Data

Jun. 1, 2010 (JP) .................................. 2010-126294

(51) Int. Cl.
*A61B 3/14* (2006.01)

(52) U.S. Cl.
CPC ........................................ *A61B 3/14* (2013.01)
USPC .............................. 351/221; 351/206; 351/246

(58) Field of Classification Search
CPC ............................... A61B 5/14555; A61B 3/12
USPC ..................... 351/221, 246, 206, 205
See application file for complete search history.

(56) References Cited

U.S. PATENT DOCUMENTS

| | | | |
|---|---|---|---|
| 5,594,512 A * | 1/1997 | Yoneda et al. ................ | 351/206 |
| 5,894,337 A | 4/1999 | Okinishi et al. | |
| 6,192,269 B1 | 2/2001 | Okumura et al. | |
| 6,324,420 B1 | 11/2001 | Kishida et al. | |
| 6,494,577 B2 | 12/2002 | Iwanaga | |
| 8,356,898 B2 * | 1/2013 | Ono .............................. | 351/206 |
| 2006/0285075 A1 | 12/2006 | Matsumura | |
| 2007/0115430 A1 * | 5/2007 | Dobashi ........................ | 351/206 |
| 2011/0292338 A1 * | 12/2011 | Iwanaga ........................ | 351/206 |

FOREIGN PATENT DOCUMENTS

| | | |
|---|---|---|
| JP | 04-150831 A | 5/1992 |
| JP | 07-016206 A | 1/1995 |
| JP | 08-052114 A | 2/1996 |
| JP | 2003-070746 A | 3/2003 |
| JP | 2003-070747 A | 3/2003 |
| JP | 3630908 B2 | 3/2005 |
| JP | 2009-066109 A | 4/2009 |

* cited by examiner

*Primary Examiner* — Hung Dang
(74) *Attorney, Agent, or Firm* — Fitzpatrick, Cella, Harper & Scinto (57) ABSTRACT

In an ophthalmic apparatus, reflected light from an eye to be examined, illuminated by an observation light source emitting continuous light, is split by a light splitting unit to enter an optical viewfinder, and a fundus image where an examiner can observe the fundus is provided by the optical viewfinder. An imaging unit sets the light quantity of the observation light source by using a moving image obtained by imaging the split and reflected light. After completing the setting of the light quantity, the imaging unit moves the light splitting unit from an optical axis, illuminates the fundus by driving the imaging light source, and obtains a still image.

34 Claims, 5 Drawing Sheets

OPHTHALMIC APPARATUS AND CONTROL METHOD THEREOF

BACKGROUND OF THE INVENTION

1. Field of the Invention

This invention relates to an ophthalmic apparatus and control method thereof.

2. Description of the Related Art

Conventionally, an ophthalmic apparatus having an automatic exposure (AE) function and/or automatic focus (AF) function has needed a dedicated AE sensor or a dedicated AF sensor, and also needed a complex switching of a light path. For instance, a light source for dedicated light-exposure detection, emitting infrared light, and a photo-detector for photometry are described in Japanese Patent Laid-Open No. 04-150831 (hereafter Ref. 1), which also describes a fundus camera that detects and measures reflected light quantity of an eye to be examined illuminated by the light source for light exposure detection using the photo-detector. Further, an ophthalmic apparatus proposed in Japanese Patent Laid-Open No. 07-016206 (hereafter Ref. 2) comprises a dedicated unit for measuring a light quantity arranged on a path divided by a member of optical separation on a path of a unit for imaging eyes.

A fundus camera proposed in Japanese Patent No. 03630908 (hereafter Ref. 3) illuminates a mark plate of focusing on which a mark is formed by an optical thin film having a wavelength characteristic for only blocking infrared light on a substrate through which both visible light and infrared light pass, projects it on a fundus of an eye to be examined, and images it using an image sensing device in an observation system. Using such a fundus camera, the mark plate image and the fundus image can be obtained by using one image sensing device in an observation system.

As described above, because the contemporary ophthalmic apparatus having AE function and/or AF function needs the dedicated AE sensor as described in Ref. 1 and Ref. 2, it becomes complicated. On the other hand, the ophthalmic apparatus proposed in Ref 2 cannot measure the light quantity when an optical viewfinder is used.

Further, the portable fundus camera proposed in Ref. 3, having an observation unit for imaging and displaying both the image of the focus mark plate projected on the fundus and the observation image of the eye to be examined, is not configured to have a finder. For this reason, it may be impossible to detect a focusing status while observing a clear tested image in an optical viewfinder.

SUMMARY OF THE INVENTION

In order to solve the above problems, one of the embodiments of the present invention provides an ophthalmic apparatus, without any complexity, which enables the performing of AE detection and/or AF detection at a low cost and with high accuracy.

According to one aspect of the present invention, there is provided an ophthalmic apparatus comprising: an illuminating unit for illuminating an eye to be examined via an illumination optical system; an imaging unit for imaging a light beam reflected from the eye to be examined via an imaging optical system, wherein the eye is illuminated by the illuminating unit; and a control unit for controlling to obtain a still image of the eye to be examined by the imaging unit in the condition of the illuminating unit determined based on a moving image of the eye to be examined, which is obtained by the imaging unit.

Further features of this present invention will become apparent from the following description of exemplary embodiments with reference to the attached drawings.

DESCRIPTION OF THE EMBODIMENTS

As discussed in detail below, referring to attached drawings, several embodiments in the present invention are explained.

First Embodiment

Figure 1:
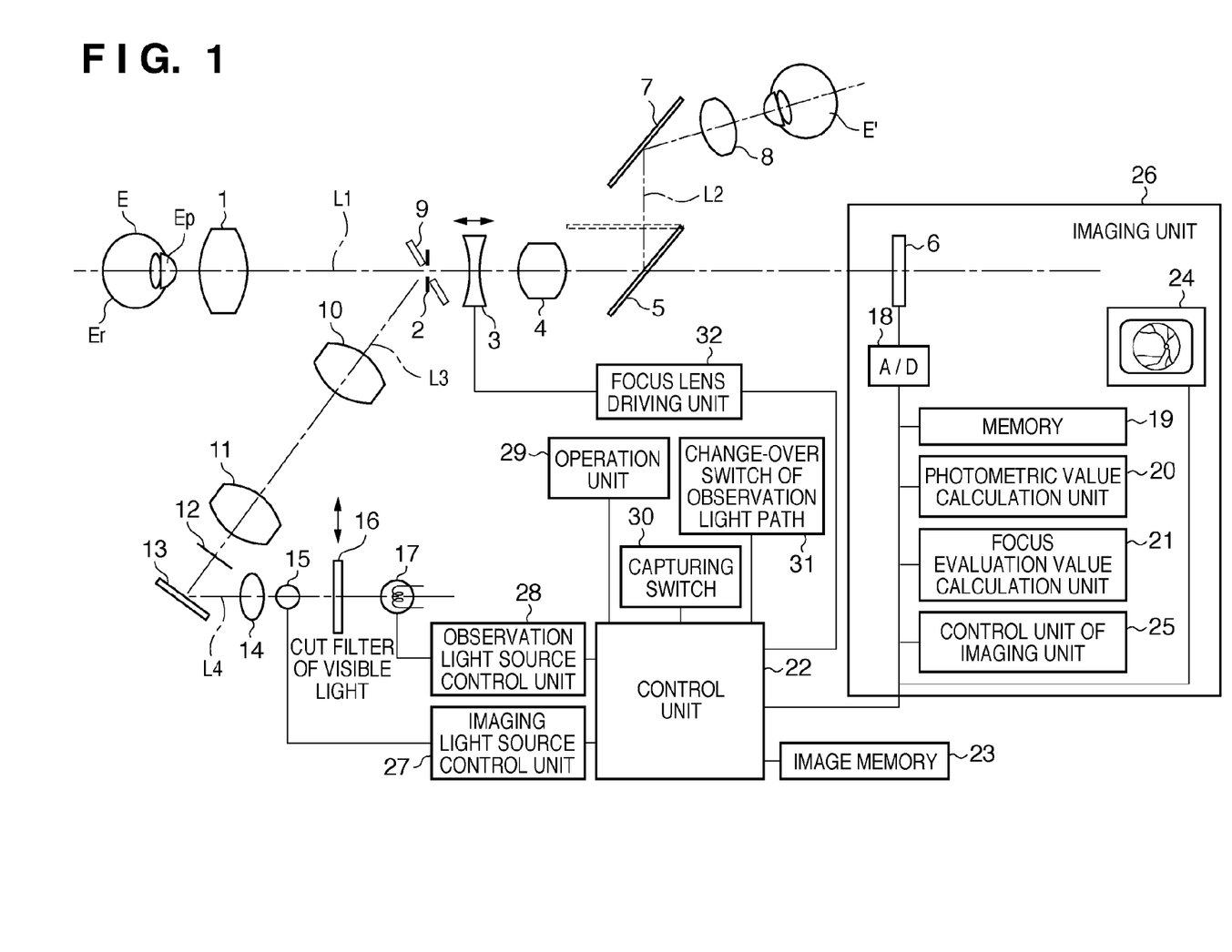
FIG. 1 shows an exemplary configuration for a fundus camera in the first embodiment.
Figure 2:
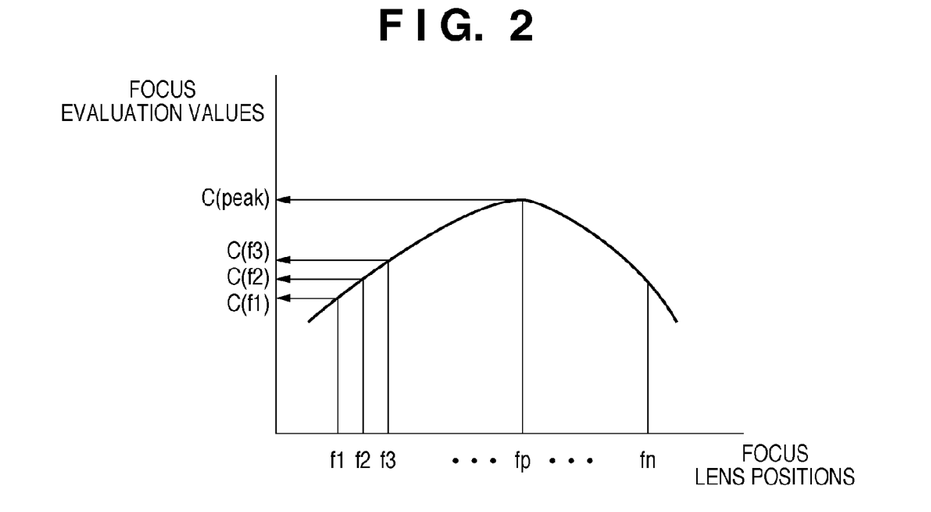
FIG. 2 shows relationship between a position of focus lens and an evaluation value.

In the first embodiment, using a fundus camera as an example, the ophthalmic apparatus has an optical viewfinder that can obtain an image and perform AE and AF detection using a shared sensor for an image of the eye to be examined, is described. FIG. 1 shows an exemplary configuration for a fundus camera in the first embodiment.

An objective lens 1 is placed corresponding to the eye E to be examined, and an imaging aperture 2, a focus lens 3, an image forming lens 4, a dichroic mirror 5 and an image sensing device 6 are disposed on an optical axis L1. As a light splitting unit, the dichroic mirror 5 is disposed on a light path along with the optical axis L1, and splits the reflected light from the eye E to travel along the direction of the optical axis L1 and the direction of the optical axis L2. Further, the image sensing device 6 has a sensitivity to visible light and infrared light. A mirror 7 and an optical viewfinder 8 are placed on the optical axis L2 in a reflecting direction of the dichroic mirror 5. An imaging optical system is configured by a set of lenses from the objective lens 1 to the image forming lens 4, and an observation system is configured by a set of lenses from the objective lens 1 to the image forming lens 4 and dichroic mirror 5, mirror 7 and an optical viewfinder 8. An observation/imaging system is configured by adding the image sensing device 6 to the above items. In addition, the dichroic mirror 5 can be moved to a dotted line in the figure by a driver of the light splitting unit, not shown in the figure. Namely, the dichroic mirror 5 is mounted so it can be put in and taken out of the path corresponding to the optical axis L1, and splits the reflected light from the eye E, illuminated by an observation light source or an imaging light source as described later, into the first light path extending in the direction of the optical axis L1 and a second light path, different from the first light path, extending in to the direction of the optical axis L2. Further, the image sensing device 6 is disposed on the first light path and the optical viewfinder 8, as described later, is disposed on the second light path.

Further, a perforated mirror 9 disposed aslant near the imaging aperture 2 and a lens 10, a lens 11, a ring aperture 12, and a mirror 13 are disposed on an optical axis L3 in the reflection direction of the perforated mirror 9. The ring aperture 12 has a ring-shaped aperture having a light blocking part at the center of the optical axis, and is allocated at an optically conjugated position of the pupil Ep of the eye E with respect to the objective lens 1, the lens 10 and the lens 11. Further, a condenser lens 14 and a strobe light source 15 emitting pulsed visible light (pulsed light) are allocated on an optical axis L4 in the reflected direction by the mirror 13. In addition, a cut filter 16 of visible light (visible light cut filter 16) is allocated so as to be put into and taken out on the path of optical axis L4, and a halogen lamp 17 as an observation light source enabling to emit normal visible and infrared light (continuous light) is also allocated on the optical axis L4. An illuminating system as a first optical system is configured to guide the light from the observation light source (halogen lamp 17) and the imaging light source (strobe light source 15) to the eye E by using these lenses from the objective lens 1 to the mirror 13 and the condenser lens 14. Further, an illuminating unit comprises this illuminating system, the strobe light source 15, the visible light cut filter 16 and the halogen lamp 17.

Meanwhile, using the imaging optical system and the observation optical system as mentioned above, a second optical system is configured to have an automatic focus mechanism for driving the focus lens 3, and to observe and capture the reflected light from the eye E, illuminated by the illuminating unit. This second optical system guides the reflected light from the eye E to the same image sensing device 6, wherein the reflected light can be obtained using the observation light source (halogen lamp 17) and the imaging light source (strobe light source 15)

An optical unit of the fundus camera is configured by the observation/imaging unit and the illuminating unit, which are accommodated in one body. Further, the optical unit of the fundus camera is mounted on a sliding platform, not shown in the figure, and can be aligned with the eye E by operating a joystick.

In the imaging unit 26, the output of the image sensing device 6, placed on the first path as mentioned above, is signalized using an A/D converter 18 and stored in a memory 19, and the converted signal is provided to a photometric value calculation unit 20 and a focus evaluation value calculation unit 21. The memory 19, the photometric value calculation unit 20, and the focus evaluation value calculation unit 21 are respectively connected to a control unit 22 including a CPU, which controls the whole apparatus. The control unit 22 is connected to an image memory 23, which stores still images as digital images acquired by the image sensing device 6. Further, the imaging unit 26 has a monitor 24 for displaying an infrared image, a visible image and others, acquired by the image sensing device 6, and a control unit 25 of the imaging unit for control of the entire imaging unit 26. In addition, this imaging unit 26 is detachably arranged in the body of the optical unit of the fundus camera with a mount unit, not shown in the figure.

Next, the photometric value calculation unit 20 and the focus evaluation value calculation unit 21 are explained as follows. The photometrical value calculation unit 20 calculates a measured value corresponding to a predetermined region of the image sensing device 6 (for example, a predetermined center region of the image sensing device) based on information obtained by converting the visible image or the infrared image, captured by the imaging sensing device 6, to digitalized signals using the A/D converter 18, and outputs the measured value to the control unit 22. Further, the focus evaluation value calculation unit 21 calculates the contrast of the image based on information obtained by converting the visible image or the infrared image, captured by the imaging sensing device 6, to digitalized signals using the A/D converter 18, and outputs the contrast as an evaluation value, representing the focusing status, to the control unit 22.

On the other hand, the strobe light source 15 is connected to an imaging light source control unit 27, and the halogen lamp 17 is connected to an observation light source control unit 28. Further, the focus lens 3 is connected to a focus lens driving unit 32, which can drive the focus lens 3 along with the direction of the light axis. The imaging light source control unit 27, the observation light source control unit 28 and the focus lens driving unit 32 are respectively connected to the control unit 22. In addition, the control unit 22 is connected to an operation unit 29, which sets an observation light quantity (amount emitted by the observation light source), an imaging light quantity (amount of emitted by the imaging light source) and others, a capturing switch 30 and a change-over switch 31 of the observation light path.

Figure 4:
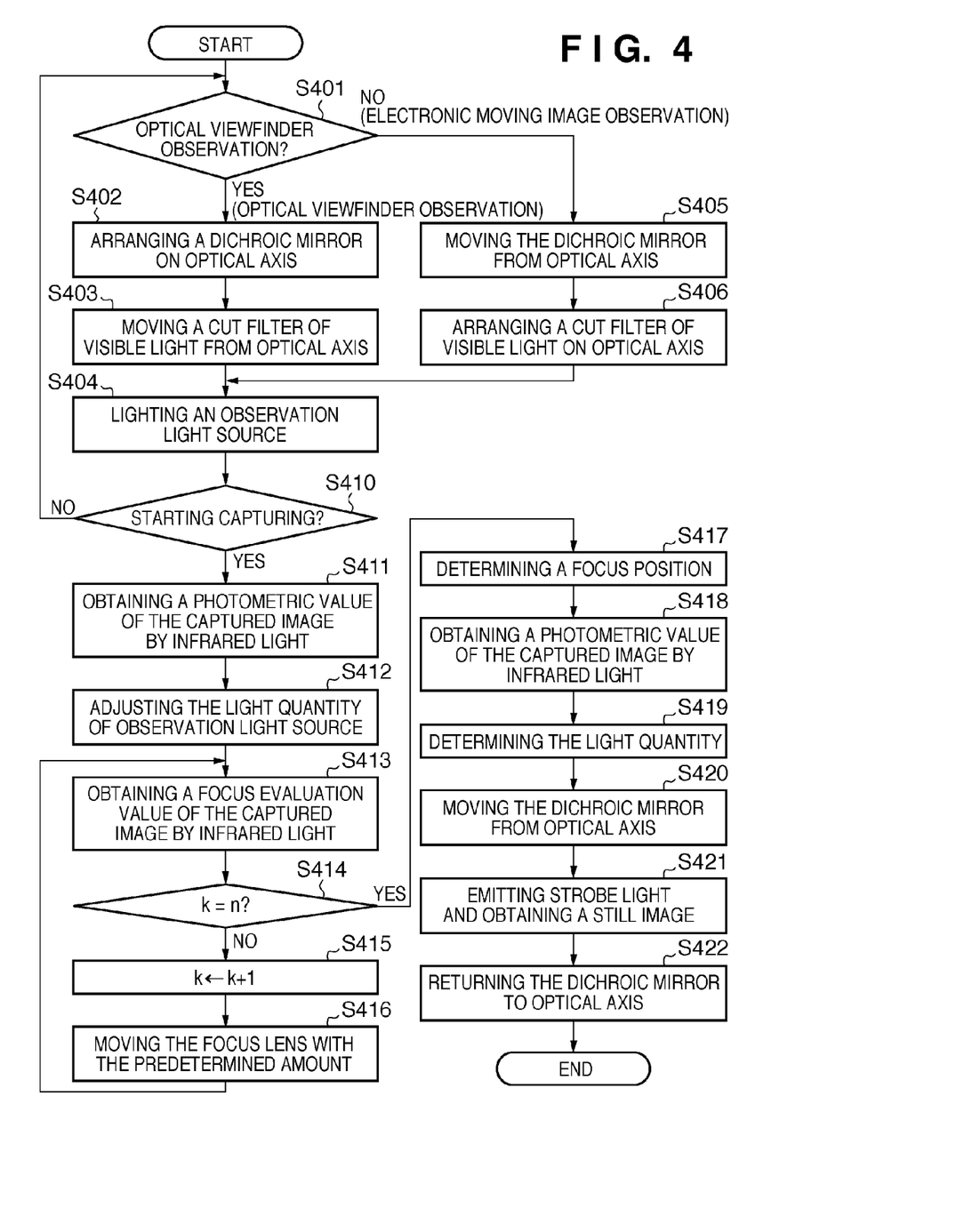
FIG. 4 shows a flowchart for explaining operations of the fundus camera in the first embodiment.

Next, referring to a flowchart of FIG. 4, the operation of capturing is explained when visible light through a viewfinder is observed in the fundus camera of this embodiment.

Using the change-over switch 31, a user can select "optical viewfinder observation" to observe a fundus illuminated by an observation light through a viewfinder, or "electronic moving image observation" to observe a moving image using the monitor 24. If the user selects "optical viewfinder observation" using the change-over switch 31 of the observation light path, then the control unit 22 may insert the dichroic mirror 5 on the optical axis L1 (Step S401 and Step S402). Further, the control unit 22 sets the visible light cut filter 16 in the state of separating from the optical axis L4 (Step S403), and lights up the halogen lamp 17 which is an observation light source (Step S404).

The light emitted from the halogen lamp 17 passes through the strobe light source 15 and it is collected by the condenser lens 14. After it is reflected by the mirror 13, its beam is constrained in a ring shape by the ring aperture 12. The light constrained by the ring aperture 12 forms an image of the ring aperture 12 on the perforated mirror 9 through the lens 11 and lens 10. This image is reflected toward the optical axis L1 by the perforated mirror 9, and again forms the image of the ring aperture 12 near the pupil Ep of the eye E, by which the fundus Er of the eye E is illuminated. At the same time, the fundus Er of the eye E is illuminated by the observation light including visible light and infrared light because the visible light cut filter 16 is moved from the optical axis L4.

A light beam (hereafter, a reflected light) exits the eye E from the pupil Ep, wherein the light beam is reflected and scattered from the fundus Er, which is illuminated by the halogen lamp 17 emitting normal light. Further, the reflected light reaches the dichroic mirror 5 through the objective lens 1, the imaging aperture 2, the focus lens 3 and the image forming lens 4. Herein, the reflected light contains visible light and infrared light, and the visible light is reflected toward the path of the optical axis L2 (second light path) and the infrared light reaches the image sensing device 6 after passing through the dichroic mirror 5 (via the first light path).

The visible reflected light from the fundus Er, which is reflected from the dichroic mirror 5 and biased toward the optical axis L2, is split to the second light path and reaches the optical viewfinder 8 via the mirror 7, and then it is observed as a fundus image of the eye E by the eye of an examiner E'. An operator aligns the eye E with the optical unit of the fundus camera by observing the eye E through the optical viewfinder 8 and operating the joystick not shown in the figure. Further, the operator pushes the capturing switch 30 after completing the alignment. The control unit 22 starts the operation of capture indicated in the steps after Step S411 when the capturing switch 30 is pushed (Step S410). Meanwhile, the above steps (Step S401 to Step S404) are repeated until the capturing switch 30 is pushed.

The control unit 22 sends a request of a measured value and a focus evaluation value to the control unit 25 of the imaging unit 26 after the capturing switch 30 is pushed. Corresponding to the request, the control unit 25 controls the image sensing device 6 to capture the infrared reflected light from the fundus Er, which is acquired by irradiating the eye with the observation light emitted from the halogen lamp 17. The control unit 25 controls the memory 19 to temporarily store the digital data obtained by digitalizing the image signal from image sensing device 6 with the A/D converter 18.

Next, the control unit 25 of the imaging unit 26 outputs a photometrical value of the fundus image E1 and contrast of the fundus image to the control unit 22, wherein using the digital data temporarily stored in the memory 19, the photometrical value of the fundus image E1 is calculated by the photometrical value calculation unit 20 and the contrast of the fundus image is calculated by the focus evaluation value calculation unit 21.

In this way, the control unit 22 receives the photometrical value of the fundus image E1 from the control unit 25 corresponding to the capturing switch 30 pushed down (Step S410, Step S411), and the light quantity is adjusted based on the received photometrical value (Step S412). For instance, the control unit 22 determines whether or not the received photometrical value E1 is within the predetermined level, and controls the observation light source control unit 28 so that the observation image should have proper brightness if the photometrical value is far less than or too large than the predetermined level. Further, the control unit 22 obtains the focus evaluation value at a current position of the focus lens 3 from the control unit 25 of the imaging unit 26 (Step S413). Furthermore, the control unit 22 controls the focus lens driving unit 32 to sequentially move the focus lens 3 to each of the positions, f1, f2, . . . , fn every if along the optical axis (Step S416). In this manner, the control unit 22 obtains the focus evaluation value C(fk) (k=1, 2, . . . , n) corresponding to each of the positions of the focus lens. Thus the control unit 22 repeats the control of focus lens driving unit 32 and the calculation of the focus evaluation value, and obtains the number n of the focus evaluation values, C(f1), C(f2), C(f3), . . . C(fn) (Step S413, Step S414, Step S415, Step S416). Further, after the control unit 22 obtains the peak value C (peak) of the focus evaluation values, it determines the position provided by the peak value C (peak) as an automatic focus position, and then it controls the focus lens driving unit 32 to move the focus lens 3 to the aforementioned position (Step S417).

After the control of driving the focus lens is completed, the control unit 22 receives the photometrical value calculated by the photometric value calculation unit 20 (Step S418), and determines the imaging light quantity based on the photometrical value and control status of the observation light source control unit 28 (Step S419). After determining the imaging light quantity, the control unit 22 controls a driving unit of the light splitting, not shown in the figure, to move the dichroic mirror 5 to the position indicated by the dashed line in the figure (Step S420). Further, the control unit 22 controls the imaging light source control unit 27 so that the strobe light source 15 emits light to illuminate the fundus Er, and the imaging unit 26 takes a visible still image (Step S421). After this operation, the control unit 22 returns the dichroic mirror 5 on the optical axis L1 (Step S422).

Next, in the fundus camera having an optical viewfinder of this embodiment, when the optical viewfinder is not used, the operation for observing a moving image (electronic moving image observation) displayed on the monitor 24 which is mounted on the imaging unit 26, is described. In this case, a user requests to switch from "optical viewfinder observation" to "electronic moving image observation" by using the change-over switch 31 of observation light path.

After switching from "optical viewfinder observation" to "electronic moving image observation" by using the change-over switch 31 is requested, the control unit 22 controls the driving unit of light split unit to move the dichroic mirror 5 to the position indicated by the dotted line in the figure (Step S401, Step S405). Further, the control unit 22 inserts the visible light cut filter 16 on the optical axis L4 (Step S406) and lights up the halogen lamp 17 (Step S404).

The light emitted from the halogen lamp 17 passes through the visible light cut filter 16 and only infrared light is selected by the wave length. After it is transmitted through the strobe light source 15, collected by the condenser lens 14 and reflected by the mirror 13, its beam is constrained in a ring-shape by the ring aperture 12. The light constrained in ring-shaped state by the ring aperture 12 once forms the image of the ring aperture 12 on the perforated mirror 9 through the lens 11 and the lens 10, and then it is reflected toward the direction of the optical axis L1 by the perforated mirror 9. The image light reflected toward the direction of the optical axis forms the image of the ring aperture 12 near the pupil Ep of the eye E through the objective lens 1, and illuminates the fundus Er of the eye E.

The light beam (reflected light) reflected and scattered from the fundus Er exits the eye E from the pupil Ep and reaches the image sensing device 6 through the objective lens 1, the imaging aperture 2, the focus lens 3 and the image forming lens 4. The fundus image of the infrared light from the eye E, which reaches the image sensing device 6, is captured by the image sensing device 6 and the output signal is digitalized by the A/D converter 18. The control unit 25 of the imaging unit 26 performs display-control to display this digital data as a moving image on the monitor 24. While the operations from Step S401 are repeated after deciding "No" in Step S410, the operator observes the image of the eye E by the infrared light displayed as the moving image on the monitor 24, and aligns the eye E with the optical unit of the fundus camera by operating the joystick, not shown in the figure. Further, the operator pushes the capturing switch 30 after completing the alignment.

The operations (Step S410 through Step S421) after the capturing switch 30 is pushed are as stated above. Meanwhile, Step S422 (returning the dichroic mirror 5 to the optical axis L1) is not performed if the "electronic moving image observation" is selected.

Meanwhile, although the dichroic mirror 5, which is a wavelength-division element, is used for the light splitting means for splitting the light path for the optical viewfinder 8 and the imaging unit 26 in this embodiment, a light splitting element such a half mirror can be used instead of the dichroic mirror 5. In this case, the image sensing device 6 will be allowed to have sensibility only corresponding to the visible light because the visible light is provided to the optical viewfinder 8 and the image sensing device 6. Furthermore, although the observation light source emitting continuous light and the imaging light source emitting pulsed light are configured separately, an LED, which can emit both continuous light and pulsed light, may be shared by the observation light source and the imaging light source. In this way, the configuration of the apparatus can be simplified.

In addition, the infrared light which passes through the dichroic mirror 5, reaches the image sensing device 6, in the "optical viewfinder observation". To the contrary, the infrared light which does not pass through the dichroic mirror 5, reaches the image sensing device 6 in "electronic moving image observation". Therefore, the algorithm or parameters for calculating the photometric value and the focus evaluation value may be changed by the observation mode of "optical viewfinder observation" or "electronic moving image observation". In this case, the control unit 22 notifies the photometric value calculation unit 20 and the focus evaluation value calculation unit 21 of the selected observation mode. Alternatively, the process of the photometric value calculation unit 20 and the focus evaluation value calculation unit 21 is shared by both observation modes, and how to deal the photometric value and the focus evaluation value in the control unit 22 may be changed corresponding to the selected observation mode. Further, during the optical viewfinder observation in Step S401 to Step S410 or during the electronic moving image observation, the adjustment of the light quantity of the observation light source and the adjustment of the automatic focus may be performed as explained in Step S411 to Step S417. During observation of the eye, a better observation will be realized by the adjustment of the light quantity and the adjustment of the automatic focus.

As mentioned above, according to the first embodiment, the fundus camera as the ophthalmic apparatus enables the operator to observe a clear image of the examined eye with the optical viewfinder and to realize no relative displacement between an image sensor and each detector by sharing them. Therefore, it is possible not to increase the complexity of the apparatus and is possible to realize higher accuracy in AE and AF detection without increasing the complexity of the apparatus and the cost. Further, according to the first embodiment, the fundus camera is configured to observe a clear image of the examined eye with the optical viewfinder with visible light, and does not irradiate the examined eye with more light than necessary because the photometric value and the focus evaluation value are calculated using infrared light not used for the visible observation. Furthermore, this structure can avoid energy consumption. When the moving image observation is performed by the monitor 24 without the optical viewfinder 8, the fundus camera can share the image sensor as detectors for detecting signals of AE and AF. Therefore, this structure realizes no relative displacement between detectors, and also higher accuracy in AE and AF detection without increasing the complexity of the apparatus and the cost. Further, this structure enables the observation of the examined eye by two methods; the optical viewfinder observation by visible light and the moving image observation by infrared light.

Second Embodiment

Figure 3:
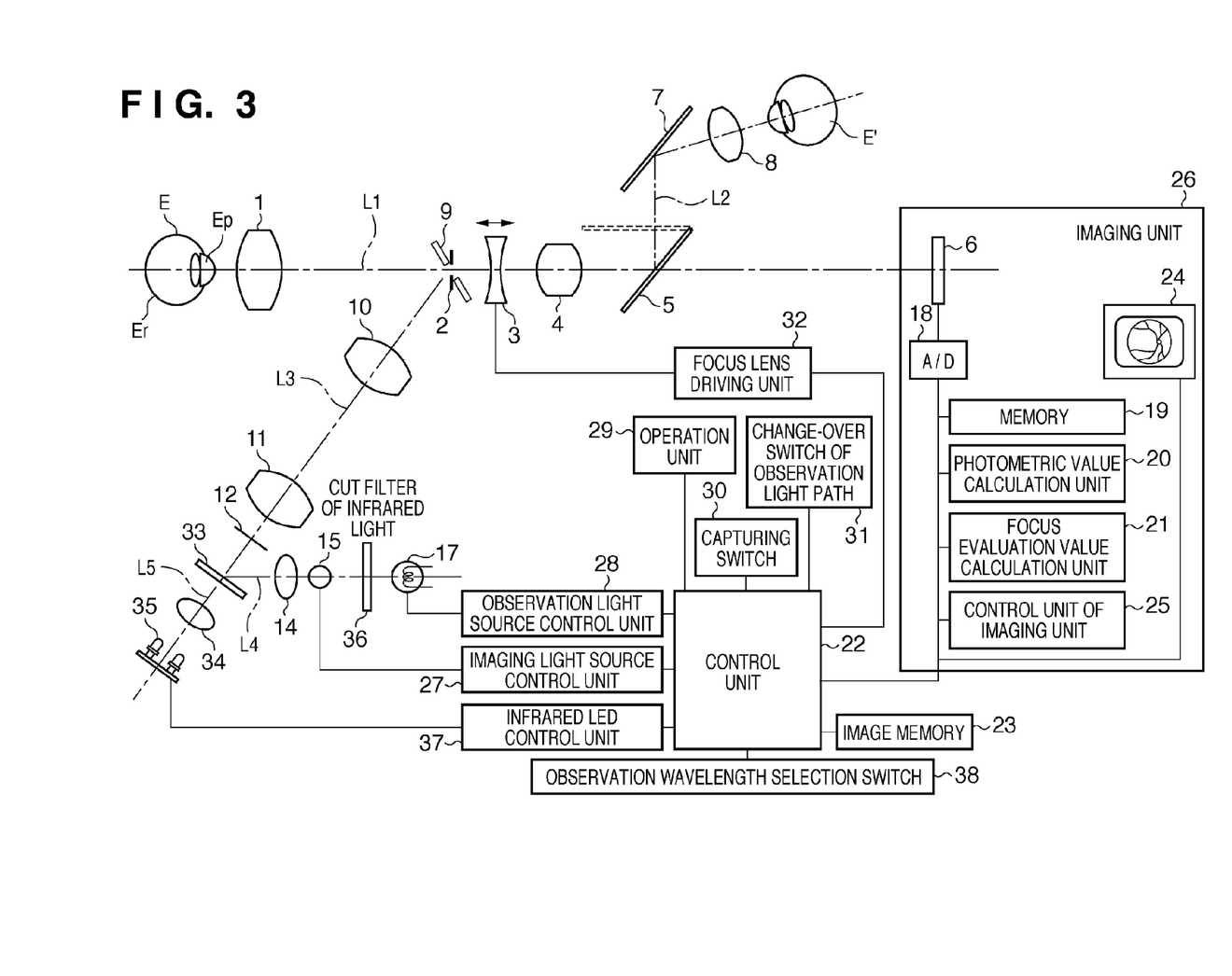
FIG. 3 shows an exemplary configuration for a fundus camera in the second embodiment.

In the second embodiment, in addition to "optical viewfinder observation" with visible light and "electronic moving image observation" with infrared light as described above, a fundus camera enabling "electronic moving image observation" by visible light is described. FIG. 3 shows an exemplary configuration for a fundus camera in the second embodiment. Elements of the structure in FIG. 3, having the same symbols in FIG. 1 refer to the same elements of the structure from the first embodiment.

In the fundus camera in the second embodiment, a cold mirror 33 having characteristic of reflecting visible light and passing infrared light therethrough is used instead of mirror 13, which is arranged in the illuminating optical system in the first embodiment. A condenser lens 34 and an infrared LED 35 including a plurality of LEDs emitting continuous infrared light are arranged on an optical axis L5 toward the passing direction of the cold mirror 33. On the other hand, the condenser lens 14 and the strobe light source 15 emitting pulsed visible light as an imaging light source are arranged on the optical axis L4 toward the reflective direction of the cold mirror 33. Further, a cut filter 36 of infrared light (infrared light cut filter 36) having the characteristic of absorbing or reflecting infrared light and the halogen lamp 17 emitting continuous light as an observation light source are arranged on the optical axis L4. A first light source emitting continuous visible light is provided by using the halogen lamp 17 and the infrared light cut filter 36. Further, a second light source emitting continuous infrared light is provided by using the infrared LED 35. Furthermore, the infrared LED 35 is connected to an LED control unit 37, and the LED control unit 37 is connected to the control unit 22. Then the control unit 22 is connected to an observation wavelength selection switch 38.

Figure 5:
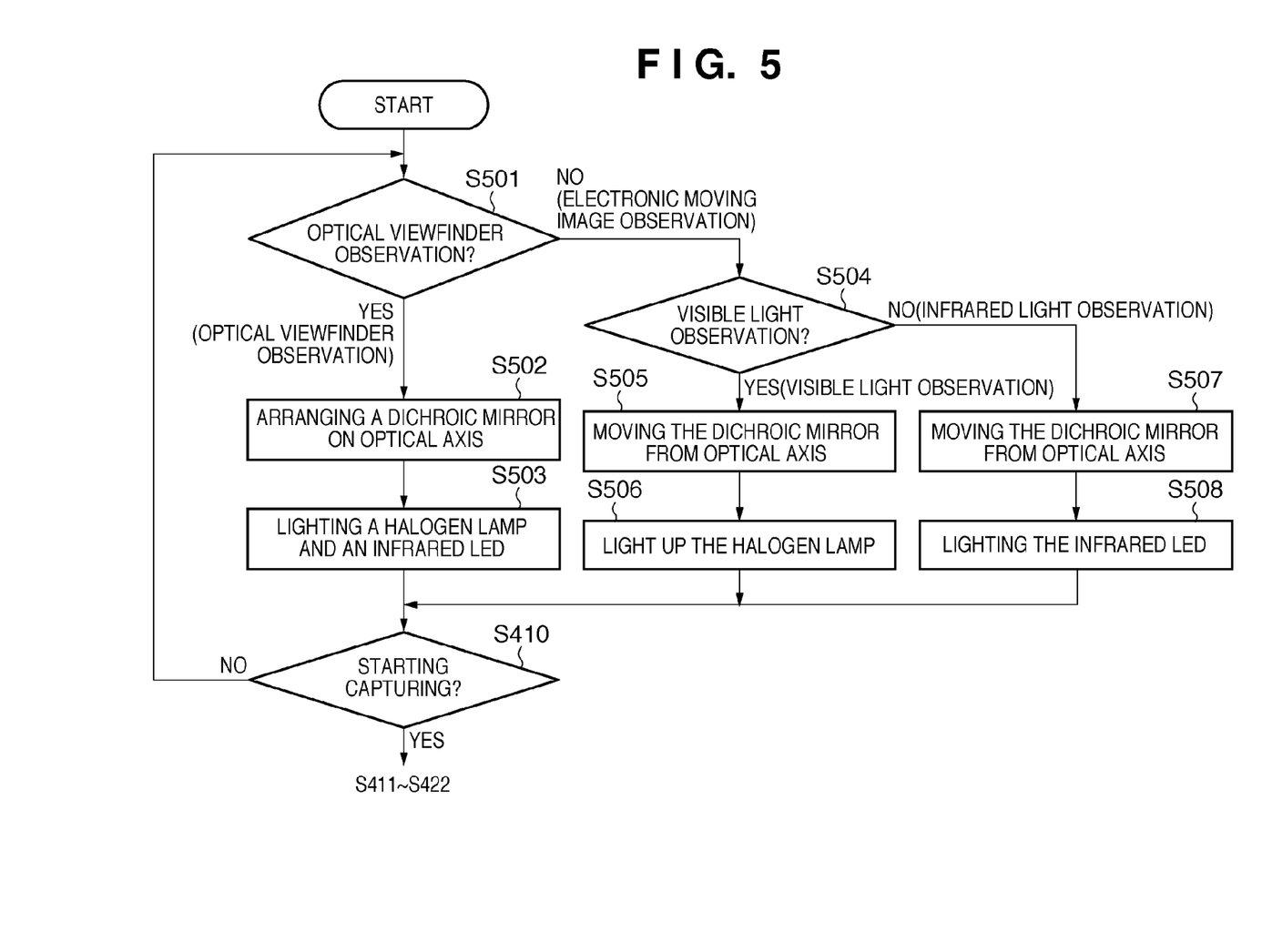
FIG. 5 shows a flowchart for explaining operations of the fundus camera in the second embodiment.

First of all, the operations of the fundus camera are described when a fundus illuminated by visible light is observed through the optical viewfinder. If the "optical viewfinder observation" is selected by using the change-over switch 31 of observation light path, the control unit 22 inserts the dichroic mirror 5 on the optical axis L1 (Step S501, Step S502). Further, the control unit 22 lights up the halogen lamp 17 and the infrared LED 35 regardless of the status of the observation wavelength selection switch 38 (Step S503).

Only visible light of the light emitted from the halogen lamp 17 is selected through the infrared light cut filter 36, and passes through the strobe light source 15. Then the visible light is collected by the condenser lens 14 and reflected by the cold mirror 33. After that, the visible light from the halogen lamp 17 is constrained in a ring-shape by the ring aperture 12. The light constrained by the ring aperture 12 forms an image of the ring aperture 12 on the perforated lens 9 through the lens 11 and lens 10. Further, this image is reflected toward the optical axis L1 by the perforated mirror 9, and again forms the image of ring aperture 12 near the pupil Ep of the eye E, by which the fundus Er of the eye E is illuminated. On the other hand, the infrared light emitted from the infrared LED 35 is collected by the condenser lens 34, and passes through the cold mirror 33. Then, it passes on the same light path as that of the light emitted from the halogen lamp 17 and illuminates the fundus Er of the eye E.

The beam exits the eye E from the pupil Ep, wherein the beam is reflected and scattered from the fundus Er which is illuminated by the visible light from the halogen lamp 17 and the infrared light from the infrared LED 35. Further, the reflected light reaches the dichroic mirror 5 through the objective lens 1, the imaging aperture 2, the focus lens 3 and the image forming lens 4. Herein, the visible light from the halogen lamp 17 is reflected to the light path of the optical axis L2 and the infrared light from the infrared LED 35 passes toward the light path of the optical axis L1. The reflected visible light from the fundus Er is reflected from the dichroic mirror 5 and deflected to the optical axis L2 and reaches the optical viewfinder 8 via the mirror 7. Then the fundus image of the eye E is observed. Further, the reflected infrared light from the fundus Er that passes through the dichroic mirror 5 on the optical axis L1 reaches the image sensing device 6.

The operator aligns the eye E with the optical unit of the fundus camera by observing the eye E through the optical viewfinder 8 and operating the joystick, not shown in the figure. The operator pushes the capturing switch 30 after completing the alignment. The operations described in the above steps, Step S410 through Step S422 in FIG. 4 are performed after the capturing switch 30 is pushed. Then the control unit 22 determines a focus position by the infrared light and the light quantity of the imaging light source (strobe light source 15), and obtains a still image by using imaging light by the strobe light source 15. In addition, although the infrared light emitted from the halogen lamp 17 is used to determine the focus position and the light quantity of the imaging light source in the first embodiment, the infrared light emitted from the infrared LED 35 is used in the second embodiment.

Next, the operations of observing the fundus illuminated by the visible light as a moving image displayed on the monitor are described. Thus, the operations are described when "electronic moving image observation" is selected by the change-over switch 31 of observation light path and "visible light observation" is selected by the observation wavelength selection switch 38.

When the light path of the imaging unit is selected to be the "electronic moving image observation" by the change-over switch 31 of observation light path, and when the visible light observation is selected by the observation wavelength selection switch 38, the control unit 22 controls the apparatus so as to move the dichroic mirror 5 to the position indicated by the dotted line in the figure (Step S501, Step S504 and Step S505). Further, the control unit 22 lights the halogen lamp 17 (Step S506).

Only visible light of the light emitted from the halogen lamp 17 is selected by wavelength through the cut filter of infrared light 36, and it passes through the strobe light source 15 and is collected by the condenser lens 14. Further, after this visible light is reflected from the cold mirror 33, it is constrained in a ring-shape by the ring aperture 12. The light constrained by the ring aperture 12 forms an image of the ring aperture 12 on the perforated mirror 9 through lens 11 and lens 10. Further, it is reflected toward the optical axis L1 by the perforated mirror 9, and again forms the image of ring aperture 12 near the pupil Ep of the eye E through the objective lens 1, by which the fundus Er of the eye E is illuminated.

The light beam exits the eye E from the pupil Ep, wherein the light beam is reflected and scattered from the fundus Er, which is illuminated by the visible light from the halogen lamp 17, and it reaches the image sensing device 6 through the objective lens 1, the imaging aperture 2, the focus lens 3 and the image forming lens 4. The control unit 25 of the imaging unit 26 controls the image sensing device 6 to capture the reflected light from the fundus Er of the eye E, which is illuminated by the visible light, and the captured image signal by the image sensing device is converted to a digital signal with the A/D converter 18 and temporarily stored in the memory 19. The monitor 24 displays this digital data (image (fundus image) of the fundus Er of the eye E) as a moving image.

The operator aligns the eye E with the optical unit of the fundus camera by observing the fundus image of the eye E displayed on the monitor 24 and operating the joystick not shown in the figure. Further, after the alignment is completed, the operator pushes the capturing switch 30. After this operation, Step S410 and Step S411 are performed. Then the control unit 22 determines a focus position by the infrared light and light quantity of the imaging light source (strobe light source 15), and obtains a still image by using the imaging light emitted from the strobe light source 15. In this regard, instead of using the infrared light, the visible light emitted from the observation light source (halogen lamp 17 and cut filter of infrared light 36), is used in Step S411, Step S413 and Step S418, and the photometric value and the focus evaluation value are respectively calculated by the photometric value calculation unit 20 and the focus evaluation value calculation unit 21.

Meanwhile, in the control unit 22 and/or the photometric value calculation unit 20 and the focus evaluation value calculation unit 21, the parameters or algorithm for calculating the photometric value and the focus evaluation value may be changed if using the infrared light or the visible light. For instance, the parameters are set so as to absorb the sensitivity difference of the image sensing device 6 to the visible light and to the infrared light. When the parameters or algorithm for calculating the photometric value and the focus evaluation value are changed in the photometric value calculation unit 20 and the focus evaluation value calculation unit 21, the control unit 22 notifies the photometric value calculation unit 20 and the focus evaluation value calculation unit 21 of whether the "electronic moving image observation" is performed by the visible light or the infrared light. Further, as described in the first embodiment, Step S422 (returning the dichroic mirror 5 to the optical axis L1) is not performed if "electronic moving image observation" is selected.

Next, the operations of the fundus camera are described when the fundus illuminated by infrared light is observed as a moving image on the monitor. Thus, the operations are described when the "electronic moving image observation" is selected by the change-over switch 31 of observation light path and the "infrared light observation" is selected by the observation wavelength selection switch 38.

When the "electronic moving image observation" is selected by the change-over switch 31, and when the infrared light observation is selected by the observation wavelength selection switch 38, the control unit 22 controls the apparatus to move the dichroic mirror 5 to the position indicated by the dotted line in the figure (Step S501, Step S504 and Step S507). Further, the control unit 22 lights up the infrared LED 35 (Step S508).

The light emitted by the infrared LED 35 is collected by the condenser lens 34, and passes through the cold mirror 33. Then, the light is constrained in a ring-shape by the ring aperture 12. The light constrained by the ring aperture 12 forms an image of the ring aperture 12 on the perforated lens 9 through the lens 11 and the lens 10, and it is reflected toward the optical axis L1 by the perforated lens 9. This light again forms the image of the ring aperture 12 near the pupil Ep of the eye E through the objective lens 1, by which the fundus Er of the eye E is illuminated.

The light beam exits the eye E from the pupil Ep, wherein the light beam is reflected and scattered from the fundus Er, which is illuminated by the infrared light from the infrared LED 35, and it reaches the image sensing device 6 through the objective lens 1, the imaging aperture 2, the focus lens 3 and the image forming lens 4. The control unit 25 of the imaging unit 26 controls the image sensing device 6 to capture the reflected light from the fundus Er of the eye E, which is illuminated by the infrared light, and the captured image signal by the image sensing device is converted to a digital signal with the A/D converter 18 and temporarily stored in the memory 19. Further, the monitor 24 displays the digital data as a moving image of the fundus image of the fundus Er.

The operator aligns the eye E with the optical unit of the fundus camera by observing the fundus image of the eye E displayed on the monitor 24 and operating the joystick not shown in the figure. After the alignment is completed, the operator pushes the capturing switch 30. After this operation, Step S410 and Step S411 are performed. Then the control unit 22 determines a focus position based on the image obtained by the observation light (infrared light) and light quantity of the imaging light source (strobe light source 15), and obtains a still image by using the imaging light emitted from the strobe light source 15. The infrared light is provided by the observation light source (infrared LED 35). Further, as described in the first embodiment, Step S422 (returning the dichroic mirror 5 to the optical axis L1) is not performed if the "electronic moving image observation" is selected.

As mentioned above, the fundus camera as an ophthalmic apparatus according to the second embodiment realizes no relative displacement between an image sensor and each detector by sharing them even if the optical viewfinder is not used. Therefore, it is possible to not increase the complexity of the apparatus and is possible to observe the moving image of the examined eye by using visible light. Further, because it realizes the AE detection and AF detection by visible light, the accuracy of the AE detection and AF detection can be enhanced at a low cost compared to that of the AE detection and AF detection by infrared light. According to the second embodiment, it enables the operator to observe the examined eye by three methods, the optical viewfinder observation by visible light, the moving image observation by visible light and the moving image observation by infrared light.

In addition, while the operations in FIG. 5 are repeated after deciding "No" in Step S410, the adjustment of the light quantity of the observation light source and the adjustment of the automatic focus may be performed, as explained in Step S411 through Step S417. The better image can be observed by using the optical viewfinder observation and the electronic moving image observation.

Further, although the observation light source (halogen lamp 17 and cut filter of infrared light 36) emitting visible light and the observation light emitting infrared light source are used in the second embodiment, light sources are not only limited to these light sources. A structure of combining the halogen lamp 17 and the cut filter 16 of visible light can be used as the observation light source emitting infrared light. In this case, the following operations can be applied:

when the optical viewfinder observation is selected, the halogen lamp 17 is lit up after the cut filter 36 of infrared light and the cut filter 16 of visible light are moved from the optical axis in Step S503.

when the electronic moving image observation by visible light is selected, the halogen lamp 17 is lit up after the cut filter 36 of infrared light is arranged on the optical axis in Step S506.

when the electronic moving image observation by infrared light is selected, the halogen lamp 17 is lit up after the cut filter 16 of visible light is arranged on the optical axis in Step S508.

As the embodiments are described in detail, the present invention can be applied to various embodiments, such as a system, apparatus, method, program or storage medium and others. To be more precise, the present invention may be applied to the system comprising a plurality of apparatuses, or the system comprising one apparatus.

According to the present invention, the ophthalmic apparatus, which enables the operator to perform AE detection and/or AF detection at a low cost and with high accuracy without any complexity, can be provided.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-126294, filed Jun. 1, 2010, which is hereby incorporated by reference herein in its entirety.

What is claimed is:

1. An ophthalmic apparatus comprising:
an illuminating unit configured to illuminate an eye to be examined via an illumination optical system;
an imaging unit configured to image a light beam reflected from the eye to be examined, illuminated by said illuminating unit, via an imaging optical system; and
a control unit configured said apparatus to control to obtain a still image of the eye to be examined by said imaging unit under a condition of said illuminating unit that is determined based on a moving image of the eye to be examined, which is obtained by said imaging unit.

2. The ophthalmic apparatus according to claim 1, further comprising a light splitting unit inserted into an optical path of the imaging optical system and configured to guide a part of the reflected beam to an optical viewfinder in the case of obtaining a moving image, and wherein said light splitting unit is removed from the optical path of the imaging optical system in the case of obtaining a still image.

3. The ophthalmic apparatus according to claim 1, further comprising a determining unit configured to determine the condition of said illuminating unit based on the moving image,
wherein said control unit controls said illuminating unit such that said imaging unit obtains a still image by imaging the eye under the determined condition.

4. An ophthalmic apparatus comprising:
an illumination unit having an observation light source generating continuous observation light, an imaging light source generating pulsed visible light, and a first optical system guiding light of said observation light source and said imaging light source to an eye to be examined;
an imaging unit configured to image the eye to be examined, illuminated by said illumination unit;
a second optical system configured to guide reflected light from the eye to be examined, which is illuminated by said illumination unit, to said imaging unit;
a light splitting unit, configured to split the reflected light into a first light path extending to said imaging unit in the direction of the optical axis and a second light path having a direction different from the direction of the first light path;
an optical viewfinder arranged on the second light path, configured to observe an illuminated eye to be examined;
a setting unit configured to set a light quantity of the imaging light source irradiating the eye to be examined with the observation light and using a moving image imaged by said imaging unit; and
a driving unit configured to, after said setting unit sets the light quantity, drive said imaging unit to capture a still image.

5. The ophthalmic apparatus according to claim 4, wherein the observation light source continuously emits the observation light including visible light and infrared light, and said light splitting unit splits infrared light included in the observation light into the first light path and splits visible light included in the reflected light into the second light path, and said setting unit sets the light quantity of the imaging light source based on the moving image obtained by said imaging unit detecting the infrared light.

6. The ophthalmic apparatus according to claim 4, further comprising:
a selecting unit configured to select observation light including both visible light and infrared light or observation light including only infrared light from the observation light source and provide the selected observation light to said first optical system; and
a display control unit configured to display the moving image obtained by said imaging unit while said selecting unit provides the observation light including only infrared light to the first optical system.

7. The ophthalmic apparatus according to claim 6, wherein the observation light source emits continuous observation light including visible light and infrared light, and
said selecting unit provides observation light including only infrared light from the observation light source to the first optical system using a filter.

8. The ophthalmic apparatus according to claim 6, wherein the observation light source comprises a first light source emitting observation light including only visible light and a second light source emitting observation light including only infrared light, and
said selecting unit obtains the observation light including visible light and infrared light by driving both the first light source and the second light source and obtains the observation light including only infrared light by driving only the second light source.

9. The ophthalmic apparatus according to claim 8, wherein said selecting unit further provides the observation light including only visible light to the first optical system, and
said display control unit displays the moving image obtained by said imaging unit while said selecting unit provides the observation light including only visible light to the first optical system.

10. The ophthalmic apparatus according to claim 4, wherein the second optical system further comprises an automatic focus mechanism, and said setting unit sets a position of the automatic focus mechanism by using the moving image.

11. The ophthalmic apparatus according to claim 4,
wherein said light splitting unit is removably arranged on the optical axis of the second optical system,
wherein said setting unit sets the light quantity of the imaging light source by inserting said light splitting unit on the optical axis of the second optical system, irradiating the eye to be examined with the observation light, and using a moving image imaged by said imaging unit, and
wherein said driving unit removes said light splitting unit from the optical axis of the second optical system after said setting unit sets the light quantity and then, drives said imaging unit to capture a still image.

12. A method of controlling an ophthalmic apparatus comprising:
an illuminating step of illuminating an eye to be examined via an illumination optical system;
an imaging step of imaging a light beam reflected from the eye to be examined, illuminated by said illuminating step, via an imaging optical system; and
a control step of controlling the apparatus to obtain a still image of the eye to be examined in said imaging step under a condition of said illuminating step that is determined based on a moving image of the eye to be examined, which is obtained in said imaging step.

13. The method according to claim 12, further comprising a determining step of determining the condition of said illuminating step based on the moving image,
wherein said control step controls said illuminating step such that a still image is obtained in said imaging step by imaging the eye under the determined condition.

14. A non-transitory computer readable storage medium storing a program causing a computer to execute the steps of the method according to claim 12.

15. A method of controlling an ophthalmic apparatus comprising: an illumination unit having an observation light source generating continuous observation light, an imaging light source generating pulsed visible light, and a first optical system guiding the light of said observation light and said imaging light source to an eye to be examined; an imaging unit for imaging the eye to be examined, illuminated by said illumination unit; a second optical system for guiding reflected light from the eye to be examined which is illuminated by said illumination unit, to said imaging unit; a light splitting unit, for splitting the reflected light into a first light path extending to said imaging unit in the direction of the optical axis and a second light path having a direction different from the direction of the first light path; and an optical viewfinder arranged on the second light path for observing an illuminated eye to be examined, said method comprising the steps of:
setting light quantity of the imaging light source, irradiating the eye to be examined with the observation light, and using a moving image imaged and acquired by said imaging unit; and
driving said imaging unit to capture a still image after said setting step sets the light quantity.

16. The method according to claim 15,
wherein said light splitting unit is removably arranged on the optical axis of the second optical system,
wherein said setting step sets the light quantity of the imaging light source by inserting said light splitting unit on the optical axis of the second optical system, irradiating the eye to be examined with the observation light, and using a moving image imaged by said imaging unit,
wherein said method further comprises a step of removing said light splitting unit from the optical axis of the second optical system after the setting in the setting step, and
wherein said driving step drives said imaging unit to capture a still image after said light splitting unit is removed from the optical axis of the second optical system.

17. A non-transitory computer readable storage medium storing a program causing a computer to execute the steps of the method according to claim 15.

18. An ophthalmic apparatus comprising:
an obtaining unit configured to obtain a photometric value based on an output of an imaging unit that obtains a moving image of an eye illuminated with infrared light;
a determining unit configured to determine, based on the photometric value obtained by said obtaining unit, an emission amount of an imaging light source used for imaging the eye with visible light; and
a control unit configured to control the imaging light source based on the determined emission amount such that a still image of the eye illuminated with the visible light is obtained.

19. The ophthalmic apparatus according to claim 18, wherein said determining unit determines an emission amount of the imaging light source based on the obtained photometric value and an emission amount of an observation light source.

20. The ophthalmic apparatus according to claim 18, wherein said obtaining unit obtains a photometric value based on an output of a portion, including a center region, of the imaging unit.

21. The ophthalmic apparatus according to claim 18, wherein, the imaging unit obtains a moving image of a fundus of the eye, and said control unit controls the imaging light source based on the determined emission amount such that a still image of the fundus of the eye is obtained.

22. The ophthalmic apparatus according to claim 18, wherein
the imaging unit has sensitivity of infrared light and visible light, and
said control unit controls the imaging light source based on the determined emission amount such that the still image is obtained by imaging the eye illuminated with the visible light using the imaging unit.

23. A control method of an ophthalmic apparatus, comprising:
an obtaining step of obtaining a photometric value based on an output of an imaging unit that obtains a moving image of an eye illuminating with infrared light;
a determining step of determining, based on the photometric value obtained in said obtaining step, an emission amount of an imaging light source used for imaging the eye with visible light; and
a control step of controlling the imaging light source based on the determined emission amount such that a still image of the eye illuminated with the visible light is obtained.

24. A non-transitory computer readable storage medium storing a program causing a computer to execute the steps of the processing method according to claim 23.

25. The method according to claim 23, wherein said determining step determines an emission amount of the imaging light source based on the obtained photometric value and an emission amount of an observation light source.

26. The method according to claim 23, wherein said obtaining step obtains a photometric value based on an output of a portion, including a center region, of the imaging unit.

27. The method according to claim 23, wherein, the imaging unit obtains a moving image of a fundus of the eye, and said control step controls the imaging light source based on the determined emission amount such that a still image of the fundus of the eye is obtained.

28. The method according to claim 23, wherein
the imaging unit has sensitivity to infrared light and visible light, and
said control step controls the imaging light source based on the determined emission amount such that the still image is obtained by imaging the eye illuminated with the visible light using the imaging unit.

29. An ophthalmic apparatus comprising:
a determining unit configured to determine an emission amount of an imaging light source for imaging an eye based on an output of a portion, including a center region, of an imaging unit that obtains a moving image of an eye by illuminating the eye with light from an observation light source; and
a control unit configured to control the imaging light source based on the determined emission amount such that a still image of the eye illuminated with light from the imaging light source is obtained.

30. A control method of an ophthalmic apparatus, comprising:
a determining step of determining an emission amount of an imaging light source for imaging an eye based on output of a portion, including a center region, of an imaging unit that obtains a moving image of an eye by illuminating the eye with light from an observation light source; and
a control step of controlling the imaging light source based on the determined emission amount such that a still image of the eye illuminated with light from the imaging light source is obtained.

31. A non-transitory computer readable storage medium storing a program causing a computer to execute the steps of the method according to claim 30.

32. An ophthalmic apparatus comprising:
a determining unit configured to determine an emission amount of an imaging light source for imaging a fundus of an eye with visible light based on an output of an imaging unit that obtains a moving image of the fundus illuminated with infrared light; and
a control unit configured to control the imaging light source based on the determined emission amount such that a still image of the eye illuminated with the visible light is obtained.

33. A control method of an ophthalmic apparatus, comprising:
a determining step of determining an emission amount of an imaging light source for imaging a fundus of an eye with visible light based on an output of an imaging unit that obtains a moving image of the fundus illuminated with infrared light; and
a control step of controlling the imaging light source based on the determined emission amount such that a still image of the eye illuminated with the visible light is obtained.

34. A non-transitory computer readable storage medium storing a program causing a computer to execute the steps of the method according to claim 33.

* * * * *